United States Patent [19]

Warner

[11] 4,418,700

[45] Dec. 6, 1983

[54] METHOD AND APPARATUS FOR MEASUREMENT OF HEART-RELATED PARAMETERS

[75] Inventor: Glenfield Warner, St. Laurent, Canada

[73] Assignees: Sylvia Warner, St. Laurent; Thiagas S. Sankar, Brossard, both of Canada

[21] Appl. No.: 242,568

[22] Filed: Mar. 11, 1981

[51] Int. Cl.³ .............................................. A61B 5/02
[52] U.S. Cl. .................................... 128/694; 128/672
[58] Field of Search ....................... 128/672, 687–690, 128/665–666, 713

[56] References Cited

U.S. PATENT DOCUMENTS

| | | | |
|---|---|---|---|
| 3,908,639 | 9/1975 | McIntyre | 128/713 |
| 3,920,004 | 11/1975 | Nakayama | 128/691 |
| 4,030,485 | 6/1977 | Warner | 128/2.05 A |
| 4,137,910 | 2/1979 | Murphy | 128/713 |
| 4,203,451 | 5/1980 | Panico | 128/672 |

FOREIGN PATENT DOCUMENTS 728833 4/1980 U.S.S.R. .............................. 128/691

OTHER PUBLICATIONS

Dimmich, R. F. et al., "Physiologic Monitor System" IBM Tech Disclosure Bulletin, vol. 19, #3, pp. 776–778, Aug. 1976.

Devi, V. et al., "A Processing System for Automatic On-Line Determination of LVET", Conf: Proc of the IFIP-IMIA(TC4) Conf. Rome Italy (6-8 Feb. 1980), pp. 167–173.

Dhupar, K. et al., "A µP-Based VFA", Conf: IEEE 1979 Frontiers of Engrg in Health Care Conf., Denver Co (6–7 Oct. 1979) pp. 145–149.

Primary Examiner—Kyle L. Howell
Assistant Examiner—Francis J. Jaworski
Attorney, Agent, or Firm—Fleit, Jacobson, Cohn & Price

[57] ABSTRACT

The invention relates to a method and apparatus for determining the magnitude of heart-related parameters in a patient. In accordance with the invention, blood volume variation of a peripheral part of the body of a patient, which variation is cyclic in nature, is detected to provide a signal representative of the blood volume. The maximum amplitude, minimum amplitude of the signal at maximum slope, the time interval between the maximum and minimum amplitudes and the instantaneous cyclic repetition rate (period) of the signal are measured, and the parameters are calculated in accordance with appropriate formulae.

26 Claims, 2 Drawing Figures

METHOD AND APPARATUS FOR MEASUREMENT OF HEART-RELATED PARAMETERS

BACKGROUND OF INVENTION

1. Field of the Invention

The invention relates to a method and apparatus for determining the magnitude of heart-related parameters in a patient.

2. Description of Prior Art

Known in the art are non-invasive methods for determining the magnitude of the heart-related parameters arterial systolic and diastolic pressure. Such a method and apparatus are taught in my U.S. Pat. No. 4,030,485. However, in this method and apparatus, it is necessary to perform a calibration procedure for each patient which is inconvenient and can lead to errors. In addition, using the methods and apparatus presently available, each heart-related parameter, such as arterial pressure, heart rate, peripheral resistance, etc., must be separately measured using separate instruments and methods. This is especially inconvenient when the parameters must be monitored remotely and on a continuous basis.

SUMMARY OF INVENTION

It is therefore an object of the invention to provide a method and apparatus for determining the magnitude of heart-related functions wherein, with a single instrument, it is possible to determine a plurality of such heart-related parameters.

It is a further object of the invention to provide such a method and apparatus normally requiring only a single factory calibration procedure.

In accordance with the invention, a method for determining the magnitude of heart-related parameters in a patient comprises: detecting blood volume variation in said patient and providing a signal representative of the amplitude of said blood volume; said blood volume variation being cyclic in nature whereby said signal comprises a cyclic curve having, in each cycle of variation, a variable slope, a maximum amplitude, a minimum amplitude, a time interval between the maximum amplitude and the minimum amplitude, and a pulse repetition period; measuring said time interval; and calculating the magnitude of selected ones of said parameters.

From a different aspect, and in accordance with the invention, an apparatus for carrying out the above method comprises: means for detecting blood volume variation in said patient and for providing a signal representative of amplitude of said blood volume; said blood volume variation being cyclic in nature whereby said signal comprises a cyclic curve having, in each cycle of variation, a variable slope, a maximum amplitude, a minimum amplitude, a time interval between said maximum amplitude and said minimum amplitude, and a pulse repetition period; means for measuring said time interval; and means for calculating the magnitude of selected ones of said parameters.

BRIEF DESCRIPTION OF DRAWINGS

The invention will be better understood by an examination of the following description, together with the accompanying drawings, in which.

DESCRIPTION OF PREFERRED EMBODIMENTS

Figure 1:
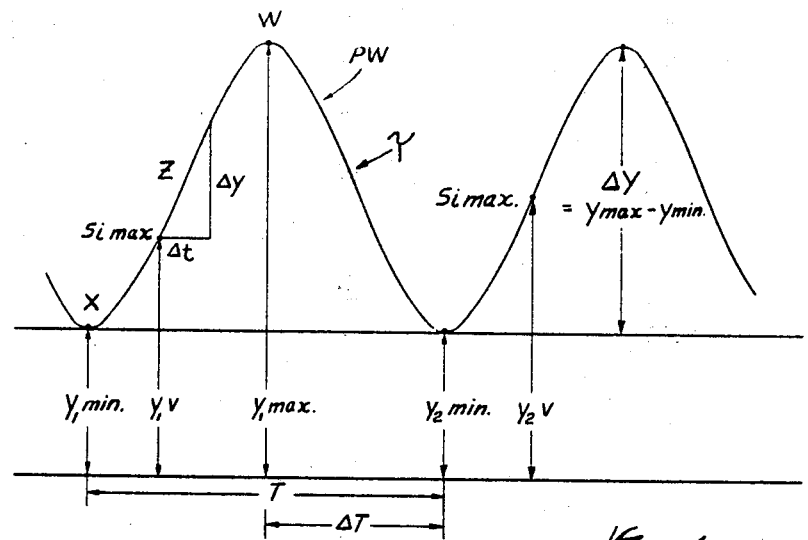
FIG. 1 is a graph useful in explaining the invention.

Referring to FIG. 1, PW is the blood volume pulse waveform as measured, for example, by a photoelectric plethysmograph as well known in the art. The X axis is in time units, and the Y axis is in electrical units such as volts.

As is known, the blood volume variation is cyclical in nature so that PW is a cyclic curve having an instantaneous cycle rate (period), a maximum amplitude, a minimum amplitude, a time interval between the maximum and minimum, and a variable slope. $Y_{iMIN}$ is the minimum amplitude of Y in the ith cycle, and $Y_{iMAX}$ is the maximum amplitude of Y in the ith cycle. $\Delta Y$ is defined as $Y_{MAX} - Y_{MIN}$, $S_i$ is the slope at any point in the ith cycle. $\Delta T_i$ is defined as the time interval between the maximum and minimum amplitudes of Y in the ith cycle, and $T_i$ is the instantaneous cycle rate (period), i.e., the cycle rate of the ith cycle or the time between the minimum of the ith cycle and the minimum of the (i+1)th cycle.

In accordance with the invention, slope is determined by the well known procedure of measuring an increment $\Delta y$ associated with a selected increment of time $\Delta t$. The value for the slope is then given by $\Delta y/\Delta t$. The procedure is performed at a plurality of points along the curve PW.

The amplitude of the signal at the point of maximum slope $S_{iMAX}$ is designated as $Y_{iV}$ for the ith cycle. In cases where measurements indicate maximum slopes at a plurality of points, the amplitudes at these points are averaged to obtain a value for $Y_{iV}$. Thus, if n points are indicated as having the same maximum slope, $Y_{iV}$ is given by $$\sum_{1}^{n} \frac{Y_{nV}}{n}$$

Now, letting $Y_{iV} - Y_{iMIN} = Y'_{iV}$ and defining $Q_i = Y'_{iV}/\Delta Y_i$ $$P_{pi} = f(Q_i)$$

where $P_{pi}$ = pulse pressure as determined by measurements in the ith cycle as discussed below.

The relationship between $P_{pi}$ and $Q_i$ depends on elastic properties of the extensible tube (in this case, an artery). A particular function for such an extensible tube is $$P_{pi} = K(Q_i/1 - Q_i) \text{ mm Hg} \tag{1}$$

where K is a constant determined by calibration as discussed below.

Thus, by determining the maximum slope, and by measuring the amplitude of Y at the point of maximum slope, and the maximum and minimum amplitudes of Y, it is possible, in accordance with the invention, to determine pulse pressure.

It is also known that $$P_p = P_s - P_d \text{ mm Hg}$$

$$e^{-\Delta T_i/\tau} = P_d/P_s \tag{2}$$

where
P_s = arterial systolic pressure;
P_d = arterial diastolic pressure; and
τ = an arterial timing constant.
τ is given by:

$$\tau = (e^{\Delta T_\tau} - 1) = f(\Delta T)$$

A particular function of ΔT which satisfies conditions for blood pressure measurements is $(\Delta T_i/a)^b \cdot \Delta T_i$ so that $$\tau_i(e^{\Delta T_i/\tau_i} - 1) = \Delta T_i \left(\frac{\Delta T_i}{a}\right)^b$$

where
$\tau_i$ is the average arterial time constant during the ith cycle; and
a and b are constants.
In a particular case, $a = 0.1$ and $b = 0.19$.

Arterial systolic pressure as determined from measurements in an ith cycle, is given by the expression:

$$P_{si} = P_{pi}/(1 - e^{-\Delta T_i/\tau_i}) + P_o \text{ mm } Hg$$

$$P_o = J(\tau) = J'(\Delta T) \tag{3}$$

A particular function J'(ΔT) which is valid is $$P_o = P_o' \left(\frac{\Delta T}{\Delta T_o}\right) \text{ mm Hg}$$

where
$P_o' = 40$ mm Hg
$T_o$ = constant = 1 sec.

Using equations 1 and 3 after obtaining the magnitude of 66 T, it is possible to obtain values for both systolic and diastolic pressure.

It is also known that instantaneous heart rate, using data obtained in the ith cycle, may be calculated using the equation:

$$HR_i = 60/T_i \text{ beats per min.}$$

Average arterial pressure during a cycle is defined as $$P_m' = (P_s + 2P_d)/3 \text{ mm, } Hg$$

$$P_m = P_m' - P_o \tag{4}$$

where $P_m'$ = effective average arterial pressure during a cycle.

Average Total Peripheral Resistance during the ith cycle is $$R_i = K_2 \sqrt{\frac{\tau_i}{W_i G_i}} \text{ } PRU \text{ units} \tag{5}$$

where $K_2$ = constant where

-continued $$G_i = \tan\frac{360(Y_{iMAX} - Y_{iV})\Delta t_i}{\Delta y_i T_i} = \tan\frac{360(Y_{iMAX} - Y_{iV})}{S_{iMAX} T_i}$$

$$W_i = \frac{2\pi}{T_i} SEC^{-1}$$

The average arterial compliance during the ith cycle is $$C_i = \frac{\tau_i}{R_i} \text{ mL/mm Hg} \tag{6}$$

The average cardiac output during the ith cycle is $$CO_i = \frac{60 P_{mi}}{R_i} \text{ liters/min.} \tag{7}$$

The average stroke volume during the ith cycle is $$SV_i = \frac{CO_i}{HR_i} (1000) \text{ mL}$$

The method of determining heart related parameters in accordance with the invention, consists of the following steps:

The calibration constant K must first be determined. As this constant need be determined only once, it does not constitute one of the steps generally involved, and the method of determining K will be more fully discussed below in the discussion of apparatus for carrying out the invention.

In any ith cycle, $Y_{iMAX}$, $Y_{iMIN}$, $\Delta T_i$, $T_i$, $S_{iMAX}$ and $Y_{iV}$ are measured. Heart related functions are then calculated with the above expressions and equations. The calculations may be performed manually, mechanically or electronically. In the electronic option, data may be fed to an appropriately programmed general purpose computer or, as per a preferred embodiment of the invention, a microcomputer may be designed to both determine slope and maximum slope, and to perform the requisite calculations.

As will be appreciated, each cycle of the signal PW constitutes a separate heart beat. Preferably, the values for the parameters are determined by taking measurements in a plurality of heart beats, obtaining values for each heart beat, and then obtaining average values. The selected heart beats may be either consecutive beats, alternating beats, or randomly selected beats.

Figure 2:
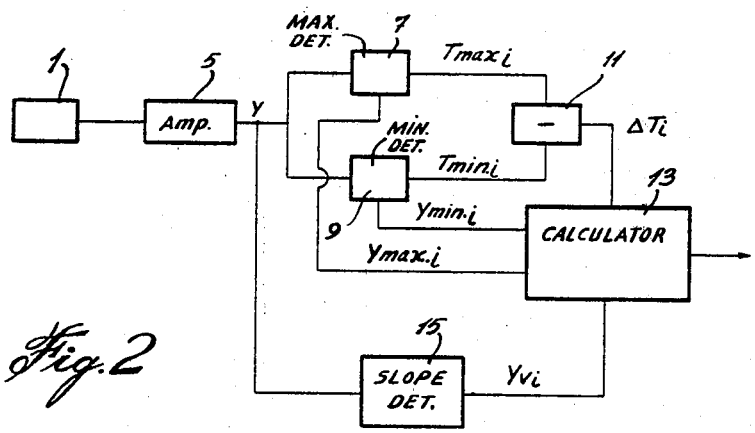
FIG. 2 is a functional block diagram of an apparatus in accordance with the invention.

Turning now to FIG. 2, 1 is a transducer for detecting blood volume in a patient and for providing an electrical signal representative of the blood volume at the output, such as, for example, a photoelectric plethysmograph. 5 is an amplifier which amplifies the output of 1 to provide at its output the varying magnitude Y. This output is fed to MAX detector 7 and MIN detector 9 which detect the maximum and minimum, respectively, of Y, and the times of occurrence thereof. The times are fed to subtractor 11 and the amplitudes are fed to calculator 13. The output of 11 is also fed to 13. It will be appreciated that the inputs to 11 could be fed directly to 13 which could perform the substraction function.

The output of 5 is also fed to a slope detector 15 which detects the maximum slope of PW and the amplitude of $Y(Y_{iV})$ associated with the maximum slope. This amplitude is also fed to 13.

The function blocks 7 to 15 may be implemented either by electronic hardware or by software in a computer or microcomputer, or a combination of both. Preferably, all of the blocks 5 to 15 are made up as a single unit including a microcomputer for the blocks 7 to 15. The single unit has an input terminal to receive an output terminal of the transducer 1, and an output means for connection to a display device. Alternatively, the display device can constitute a part of the single unit.

To calibrate the unit, $P_p$ is determined by an alternate method (using, for example, the cuff apparatus employed by physicians in examining their patients.) Measurements of maximum and minimum signal amplitudes, as well as amplitude at maximum slope, are then taken, and these amplitudes, and the value of $P_p$ are used to determine the value of K from expression (1) above. As long as the bandwidth of the amplifier 5 remains constant, the apparatus does not have to be recalibrated under normal conditions.

The unit may need to be recalibrated for a particular patient if that patient suffers from atherosclerosis or other obstructive circulatory condition. The calibration needs to be done only once during a period of time during which the energy loss due to atherosclerosis does not change substantially.

If the unit includes an automatic calculator, e.g., a microcomputer, it can be programmed to automatically perform the calibration step.

The method and apparatus above-described have been presented for the purpose of illustrating, but not limiting, the invention. Various modifications, which will come readily to the mind of one skilled in the art, are within the scope of the invention as defined in the appended claims.

I claim:

1. Apparatus for determining the magnitude of heart-related parameters in a patient;
   comprising:
   means for detecting blood volume, and thereby blood volume variation, in said patient, and for providing a signal representative of said blood volume, and thereby said blood volume variation;
   said means for detecting being attachable to said patient to thereby detect said blood volume, and thereby said blood volume variation;
   said blood volume variation being cyclic in nature whereby said signal comprises a cyclic curve having, in each cycle of variation, a variable slope, a maximum amplitude, a minimum amplitude, a time interval between said maximum amplitude and said minimum amplitude, and a pulse repetition period;
   means for measuring said time interval, said means for measuring being connected to said means for detecting; and
   means for calculating the magnitude of selected ones of said parameters, said means for calculating being connected to both said means for detecting and said means for measuring;
   wherein said selected parameter is pulse pressure and wherein the means for calculating calculates the pulse pressure in accordance with the expression:

$$P_{pi} = K\left(\frac{Q_i}{1 - Q_i}\right)$$

where
   $P_{pi}$ = pulse pressure as calculated with data obtained in said selected cycle of variation
   K = calibration constant
   $Q_i = Y'_{iV}/\Delta Y_i$
      where
      $Y'_{iV} = Y_{iV} - Y_{iMIN}$
      $Y_{iV}$ = the amplitude of said signal at the maximum value of said slope in said selected cycle of variation
      $Y_{iMIN}$ = said minimum amplitude in said selected cycle of variation;
      $\Delta Y_i = Y_{iMAX} - Y_{iMIN}$
         where
         $Y_{iMAX}$ = said maximum amplitude in said selected cycle of variation.

2. Apparatus as defined in claim 1 and further comprising:
   means for measuring said maximum and minimum amplitudes and the amplitude of said signal at the maximum value of said slope.

3. Apparatus as defined in claim 2 wherein said means for calculating comprises computer means.

4. Apparatus as defined in claim 2 wherein said means for calculating comprises a microcomputer.

5. Apparatus for determining the magnitude of heart-related parameters in a patient;
   comprising:
   means for detecting blood volume, and thereby blood volume variation, in said patient, and for providing a signal representative of said blood volume, and thereby said blood volume variation;
   said means for detecting being attachable to said patient to thereby detect said blood volume, and thereby said blood volume variation;
   said blood volume variation being cyclic in nature whereby said signal comprises a cyclic curve having, in each cycle of variation, a variable slope, a maximum amplitude, a minimum amplitude, a time interval between said maximum amplitude and said minimum amplitude, and a pulse repetition period;
   means for measuring said time interval, said means for measuring being connected to said means for detecting; and
   means for calculating the magnitude of selected ones of said parameters, said means for calculating being connected to both said means for detecting and said means for measuring;
   wherein said selected parameter in arterial systolic pressure and wherein the means for calculating calculates the systolic pressure in accordance with the expression:

$$P_{si} = \frac{P_{pi}}{1 - e^{-\Delta T_i/\tau_i}} + P_o$$

where
   $P_{si}$ = arterial systolic pressure as calculated with data obtained in said selected cycle of variation;
   $P_{pi}$ = pulse pressure as calculated with data obtained in said selected cycle of variation;
   $P_o$ = constant pressure
   $\Delta T_i$ = said time interval of said cycle; and
   $\tau_i$ is given by the implicit equation:

$$\tau_i(e^{\Delta T_i/\tau_i} - 1) = \Delta T_i \left(\frac{\Delta T_i}{a}\right)^b$$

where a and b are constants $\tau_i$ = average arterial time constant during the $i^{th}$ cycle.

6. Apparatus as defined in claim 5 and further comprising:

means for measuring said maximum and minimum amplitudes and the amplitude of said signal at the maximum value of said slope.

7. Apparatus as defined in claim 6 wherein said means for calculating comprises computer means.

8. Apparatus as defined in claim 7 wherein said means for calculating comprises a microcomputer.

9. Apparatus as defined in claim 8 wherein said selected parameter is arterial diastolic pressure and wherein the means for calculating calculates the diastolic pressure in accordance with the expression:

$$P_{di} = P_{si} - P_{pi}$$

where $P_{di}$ = arterial diastolic pressure as calculated with data obtained in said selected cycle of variation;

$P_{si}$ = arterial systolic pressure as calculated with data obtained in said selected cycle of variation; and $P_{pi}$ = pulse pressure as calculated with data obtained in said selected cycle of variation.

10. Apparatus for determining the magnitude of heart-related parameters in a patient;

comprising:

means for detecting blood volume, and thereby blood volume variation, in said patient, and for providing a signal representative of said blood volume, and thereby said blood volume variation;

said means for detecting being attachable to said patient to thereby detect said blood volume, and thereby said blood volume variation;

said blood volume variation being cyclic in nature whereby said signal comprises a cyclic curve having, in each cycle of variation, a variable slope, a maximum amplitude, a minimum amplitude, a time interval between said maximum amplitude and said minimum amplitude, and a pulse repetition period;

means for measuring said time interval, said means for measuring being connected to said means for detecting; and means for calculating the magnitude of selected ones of said parameters, said means for calculating being connected to both said means for detecting and said means for measuring;

wherein said selected parameter is average peripheral resistance and wherein the means for calculating calculates the resistance in accordance with the expression:

$$R_i = K_2 \sqrt{\frac{\tau_i}{W_i G_i}}$$

where $R_i$ = average peripheral resistance during the $i^{th}$ cycle as calculated with data obtained in said selected cycle of variation;

$K_2$ = constant $\tau_i$ is given by the implicit formula $$\tau_i \left(e^{\frac{\Delta T_i}{\tau_i}} - 1\right) = \Delta T_i \left(\frac{\Delta T_i}{a}\right)^b$$

a and b are constants $$W_i = \frac{2\pi}{T_i}$$

$$G_i = \tan \frac{360(Y_{iMAX} - Y_{iV})\Delta t_i}{\Delta y_i T_i} = \tan \frac{360(Y_{iMAX} - Y_{iV})}{S_{iMAX} T_i}$$

where $\Delta y_i$ is an incremental change in Y associated with an incremental change in $T = \Delta t$, and $S_{iMAX}$ = maximum slope in the ith cycle = $\Delta y_i / \Delta t_i$.

11. Apparatus as defined in claim 10 and further comprising:

means for measuring said maximum and minimum amplitudes and the amplitude of said signal at the maximum value of said slope.

12. Apparatus as defined in claim 11 wherein said means for calculating comprises computer means.

13. Apparatus as defined in claim 12 wherein said means for calculating comprises a microcomputer.

14. Apparatus for determining the magnitude of heart-related parameters in a patient;

comprising:

means for detecting blood volume, and thereby blood volume variation, in said patient, and for providing a signal representative of said blood volume, and thereby said blood volume variation;

said means for detecting being attachable to said patient to thereby detect said blood volume, and thereby said blood volume variation;

said blood volume variation being cyclic in nature whereby said signal comprises a cyclic curve having, in each cycle of variation, a variable slope, a maximum amplitude, a minimum amplitude, a time interval between said maximum amplitude and said minimum amplitude, and a pulse repetition period;

means for measuring said time interval, said means for measuring being connected to said means for detecting; and means for calculating the magnitude of selected ones of said parameters, said means for calculating being connected to both said means for detecting and said means for measuring;

wherein said selected parameter is arterial compliance and wherein the means for calculating calculates the arterial compliance in accordance with the expression:

$$C_i = \tau_i / R_i$$

where $C_i$ = the average arterial compliance in the $i^{th}$ cycle $$R_i = K_2 \sqrt{\frac{\tau_i}{W_i G_i}}$$

$R_i$=average peripheral resistance during the $i^{th}$ cycle as calculated with data obtained in said selected cycle of variation;

$K_2$=constant $\tau_i$ is given by the implicit formula $$\tau_i \left( e^{\frac{\Delta T_i}{\tau_i}} - 1 \right) = \Delta T_i \left( \frac{\Delta T_i}{a} \right)^b$$

a and b are constants $W_i = 2\pi/T_i$ $$G_i = \tan \frac{360(Y_{iMAX} - Y_{iV})\Delta t_i}{\Delta y_i T_i} = \tan \frac{360(Y_{iMAX} - Y_{iV})}{S_{iMAX} T_i}$$

where $\Delta y_i$ is an incremental change in Y associated with an incremental change in T=$\Delta t$, and $S_{iMAX}$=maximum slope in the ith cycle=$\Delta y_i/\Delta t_i$.

15. Apparatus as defined in claim 14 and further comprising:

means for measuring said maximum and minimum amplitudes and the amplitude of said signal at the maximum value of said slope.

16. Apparatus as defined in claim 15 wherein said means for calculating comprises computer means.

17. Apparatus as defined in claim 16 wherein said means for calculating comprises a microcomputer.

18. A method for determining the magnitude of heart-related parameters in a patient;

comprising:

detecting blood volume, and thereby blood volume variation, in said patient and providing a signal representative of said blood volume, and thereby said blood volume variation;

said blood volume variation being cyclic in nature whereby said signal comprises a cyclic curve having, in each cycle of variation, a variable slope, a maximum amplitude, a minimum amplitude, a time interval between the maximum amplitude and the minimum amplitude, and a pulse repetition period;

measuring said time interval; and calculating the magnitude of selected ones of said parameters;

wherein said selected parameter is pulse pressure which is calculated in accordance with the expression:

$$P_{pi} = K \left( \frac{Q_i}{1 - Q_i} \right)$$

where $P_{pi}$=pulse pressure as calculated with data obtained in said selected cycle of variation;

K=calibration constant $Q_i = Y'_{iV}/\Delta Y_i$ $Y'_{iV} = Y_{iV} - Y_{iMIN}$ $Y_{iV}$=the amplitude of said signal at the maximum value of said slope in said selected cycle of variation;

$Y_{iMIN}$=said minimum amplitude in said selected cycle of variation;

$\Delta Y_i = Y_{iMAX} - Y_{iMIN}$ where $Y_{iMAX}$=said maximum amplitude in said selected cycle of variation.

19. A method as defined in claim 18 and further comprising the steps of measuring said maximum and minimum amplitudes and the amplitude of said signal at the maximum value of said slope.

20. A method for determining the magnitude of heart-related parameters in a patient;

comprising:

detecting blood volume, and thereby blood volume variation, in said patient and providing a signal representative of said blood volume, and thereby said blood volume variation;

said blood volume variation being cyclic in nature whereby said signal comprises a cyclic curve having, in each cycle of variation, a variable slope, a maximum amplitude, a minimum amplitude, a time interval between the maximum amplitude and the minimum amplitude, and a pulse repetition period;

measuring said time interval; and calculating the magnitude of selected ones of said parameters;

wherein said selected parameter is arterial systolic pressure which is calculated in accordance with the expression:

$$P_{si} = \frac{P_{pi}}{1 - e^{-\Delta T_i/\tau_i}} + P_o$$

where $P_{si}$=arterial systolic pressure as calculated with data obtained in said selected cycle of variation;

$P_{pi}$=pulse pressure as calculated with data obtained in said selected cycle of variation;

$P_o$=constant pressure $\Delta T_i$=said time interval of said cycle; and $\tau_i$ is given by the implicit equation:

$$\tau_i(e^{\Delta T_i/\tau_i - 1}) = \Delta T_i \left( \frac{\Delta T_i}{a} \right)^b$$

where a and b are constants $\tau_i$=average arterial time constant during the ith cycle.

21. A method as defined in claim 20 and further comprising the steps of measuring said maximum and minimum amplitudes and the amplitude of said signal at the maximum value of said slope.

22. A method as defined in claim 21 wherein said selected parameter is arterial diastolic pressure which is calculated in accordance with the expression:

$$P_{di} = P_{si} - P_{pi}$$

where $P_{di}$=arterial diastolic pressure as calculated with data obtained in said selected cycle of variation.

23. A method for determining the magnitude of heart-related parameters in a patient;

comprising:

detecting blood volume, and thereby blood volume variation, in said patient and providing a signal representative of said blood volume, and thereby said blood volume variation;

said blood volume variation being cyclic in nature whereby said signal comprises a cyclic curve having, in each cycle of variation, a variable slope, a maximum amplitude, a minimum amplitude, a time interval between the maximum amplitude and the minimum amplitude, and a pulse repetition period; measuring said time interval; and calculating the magnitude of selected ones of said parameters;

wherein said selected parameter is total peripheral resistance which is calculated in accordance with the expression:

$$R_i = K_2 \sqrt{\frac{\tau_i}{W_i G_i}}$$

where $R_i$ = average peripheral resistance during the $i^{th}$ cycle as calculated with data obtained in said selected cycle of variation;

$K_2$ = constant $\tau_i$ is given by the implicit formula $$\tau_i \left( e^{\frac{\Delta T_i}{\tau_i}} - 1 \right) = \Delta T_i \left( \frac{\Delta T_i}{a} \right)^b$$

a and b are constants $W_i = 2\pi/T_i$ $$G_i = \tan \frac{360(Y_{iMAX} - Y_{iV})\Delta t_i}{\Delta y_i T_i} = \tan \frac{360(Y_{iMAX} - Y_{iV})}{S_{iMAX} T_i}$$

where $\Delta y_i$ is an incremental change in Y associated with an incremental change in $T = \Delta t$, and $S_{iMAX}$ = maximum slope in the $i^{th}$ cycle = $\Delta y_i/\Delta t_i$.

24. A method as defined in claim 23 and further comprising the steps of measuring said maximum and minimum amplitudes and the amplitude of said signal at the maximum value of said slope.

25. Apparatus for determining the magnitude of heart-related parameters in a patient;

comprising:

means for detecting blood volume and thereby blood volume variation, in said patient, and for providing a signal representative of said blood volume, and thereby said blood volume variation;

said means for detecting being attachable to said patient to thereby detect said blood volume, and thereby said blood volume variation;

said blood volume variation being cyclic in nature whereby said signal comprises a cyclic curve having, in each cycle of variation, a variable slope, a maximum amplitude, a minimum amplitude, a time interval between said maximum amplitude and said minimum amplitude, and a pulse repetition period;

means for measuring said time interval, said means for measuring being connected to said means for detecting; and means for calculating the magnitude of selected ones of said parameters, said means for calculating being connected to both said means for detecting and said means for measuring;

wherein said selected parameter is arterial timing constant and wherein the means for calculating calculates the arterial timing constant in accordance with the expression:

$$\tau_i(e^{\Delta T_i/\tau_i} - 1) = \Delta T_i \left( \frac{\Delta T_i}{a} \right)^b$$

where $\tau_i$ = the average arterial time constant during the $i^{th}$ cycle;

a = constant;

b = constant; and $\Delta T_i$ = said time interval between said maximum amplitude and said minimum amplitude.

26. A method for determining the magnitude of heart-related parameters in a patient;

comprising:

detecting blood volume, and thereby blood volume variation, in said patient and providing a signal representative of said blood volume, and thereby said blood volume variation;

said blood volume variation being cyclic in nature whereby said signal comprises a cyclic curve having, in each cycle of variation, a variable slope, a maximum amplitude, a minimum amplitude, a time interval between the maximum amplitude and the minimum amplitude, and a pulse repetition period;

measuring said time interval; and calculating the magnitude of selected ones of said parameters;

wherein said selected parameter is arterial timing constant and wherein the means for calculating calculates the arterial timing constant in accordance with the expression:

$$\tau_i(e^{\Delta T_i/\tau_i - 1}) = \Delta T_i \left( \frac{\Delta T_i}{a} \right)^b$$

where $\tau_i$ = the average arterial time constant during the $i^{th}$ cycle;

a = constant;

b = constant; and $\Delta T_i$ = said time interval between said maximum amplitude and said minimum amplitude.

* * * * *

UNITED STATES PATENT AND TRADEMARK OFFICE
CERTIFICATE OF CORRECTION

PATENT NO. : 4,418,700
DATED : December 6, 1983
INVENTOR(S) : Glenfield WARNER

It is certified that error appears in the above-identified patent and that said Letters Patent are hereby corrected as shown below:

Column 2, line 17, "$\Delta Y$" should read --$\Delta Y_i$--.

Column 2, line 18, "$Y_{MAX}$" should read --$Y_{iMAX}$--.

Column 2, line 18, "$Y_{MIN}$" should read -- $Y_{iMIN}$--.

Column 2, line 43, "$Q_1$" should read --$Q_i$--.

Column 8, line 17 and column 11, line 37, "Y" should read --$Y_i$--.

Column 8, line 18 and column 11, line 38, "$T=\Delta t$" should read --$T_i=\Delta t_i$--.

Column 9, line 19, "Y" should read --$Y_i$--.

Column 9, line 20, "$T=\Delta t$" should read --$T_i=\Delta t_i$--.

Signed and Sealed this

Nineteenth Day of March 1985

[SEAL]

Attest:

DONALD J. QUIGG

Attesting Officer    Acting Commissioner of Patents and Trademarks